(12) United States Patent
Ronen et al.

(10) Patent No.: US 11,147,507 B2
(45) Date of Patent: Oct. 19, 2021

(54) DECISION SUPPORT SYSTEM FOR CARDIOPULMONARY RESUSCITATION (CPR)

(71) Applicant: ORIDION MEDICAL 1987 LTD., Jerusalem (IL)

(72) Inventors: Michal Ronen, Givat-Brenner (IL); Sharon Einav, Zur Hadassah (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 525 days.

(21) Appl. No.: 15/178,396

(22) Filed: Jun. 9, 2016

(65) Prior Publication Data
US 2016/0287170 A1 Oct. 6, 2016

Related U.S. Application Data

(63) Continuation-in-part of application No. 14/171,128, filed on Feb. 3, 2014, now Pat. No. 11,026,595.

(51) Int. Cl.
*A61B 5/00* (2006.01)
*A61H 31/00* (2006.01)
(Continued)

(52) U.S. Cl.
CPC ............ *A61B 5/4848* (2013.01); *A61B 5/082* (2013.01); *A61B 5/0836* (2013.01);
(Continued)

(58) Field of Classification Search
CPC .......... A61B 5/00; A61B 5/01; A61B 5/0205; A61B 5/107; A61B 5/7235; A61B 5/7275;
(Continued)

(56) References Cited

U.S. PATENT DOCUMENTS 5,598,508 A 1/1997 Goldman
5,751,911 A 5/1998 Goldman
(Continued)

FOREIGN PATENT DOCUMENTS

WO 2011/154948 12/2011

OTHER PUBLICATIONS

Einav et al., (2011) Mathematical modeling for prediction of survival from resuscitation based on computerized continuous capnography: proof of concept. Acad Emerg Med 18(5): 468-75.
(Continued)

*Primary Examiner* — Eric J Messersmith
(74) *Attorney, Agent, or Firm* — Cantor Colburn LLP

(57) ABSTRACT

There is provided herein a decision support system for cardiopulmonary resuscitation (CPR), the system comprising: a medical monitoring device configured to produce $CO_2$ waveforms of exhaled breath of a subject undergoing CPR, and a computing unit configured to extract one or more features related to the $CO_2$ waveforms and/or a trend thereof produced by said device, obtain one or more parameters/variables selected from a group of one or more background parameters, one or more physiological variables and one or more baseline parameters related to the subject undergoing CPR, and determine effectiveness of CPR and/or CPR outcome based at least on the one or more features and/or the trend thereof and on the one or more parameters/variables.

24 Claims, 4 Drawing Sheets

(51) Int. Cl.
*A61B 5/08* (2006.01)
*G16H 40/63* (2018.01)
*A61B 5/083* (2006.01)
*G16H 20/30* (2018.01)
*A61B 5/01* (2006.01)
*A61B 5/024* (2006.01)
*A61B 5/053* (2021.01)
*A61B 5/097* (2006.01)
*A61B 5/0205* (2006.01)
*G16H 50/20* (2018.01)

(52) U.S. Cl.
CPC .......... *A61B 5/7235* (2013.01); *A61B 5/7275* (2013.01); *A61H 31/005* (2013.01); *A61H 31/006* (2013.01); *G16H 20/30* (2018.01); *G16H 40/63* (2018.01); *A61B 5/01* (2013.01); *A61B 5/024* (2013.01); *A61B 5/0205* (2013.01); *A61B 5/053* (2013.01); *A61B 5/097* (2013.01); *A61B 5/742* (2013.01); *G16H 50/20* (2018.01)

(58) Field of Classification Search
CPC ..... A61B 5/4848; A61B 5/082; A61B 5/0836; A61B 5/097; A61B 5/053; A61B 5/024; A61B 5/742; A61H 31/00; A61H 31/005; A61H 31/006; G16H 40/63; G16H 20/30; G16H 50/20
See application file for complete search history.

(56) References Cited

U.S. PATENT DOCUMENTS

| | | | |
|---|---|---|---|
| 8,000,937 | B2 | 8/2011 | Zeng Lingbo |
| 9,770,191 | B2 | 9/2017 | Colman et al. |
| 10,178,962 | B2 | 1/2019 | Colman et al. |
| 2002/0082511 | A1 | 6/2002 | Carlebach et al. |
| 2002/0177793 | A1* | 11/2002 | Sherman ............. A61H 31/008 601/41 |
| 2003/0073919 | A1 | 4/2003 | Hampton |
| 2006/0155206 | A1 | 7/2006 | Lynn |
| 2007/0191697 | A1* | 8/2007 | Lynn .................... A61B 5/0205 600/323 |
| 2008/0039735 | A1 | 2/2008 | Hickerson |
| 2009/0149723 | A1* | 6/2009 | Krauss ............... A61B 5/14552 600/301 |
| 2011/0040713 | A1 | 2/2011 | Colman |
| 2012/0016251 | A1 | 1/2012 | Zhang |
| 2012/0105485 | A1 | 5/2012 | Colman |
| 2012/0302910 | A1* | 11/2012 | Freeman ........... A61M 16/0084 600/538 |
| 2013/0324873 | A1* | 12/2013 | Babaeizadeh ........ A61B 5/4848 600/532 |
| 2015/0216447 | A1 | 8/2015 | Colman et al. |
| 2016/0128626 | A1* | 5/2016 | Johnson ............... A61H 31/005 600/301 |
| 2018/0116554 | A1 | 5/2018 | Colman et al. |

OTHER PUBLICATIONS

International Application No. PCT/IL2015/050031 Written Opinion and International Search Report dated Mar. 27, 2015, 8 pages.

* cited by examiner

DECISION SUPPORT SYSTEM FOR CARDIOPULMONARY RESUSCITATION (CPR)

RELATED APPLICATION DATA

This application is a Continuation-In-Part of U.S. patent application Ser. No. 14/171,128, filed Feb. 3, 2014 (published as US 20150216447), the contents of which are hereby incorporated by reference in its entirety.

TECHNICAL FIELD

The present disclosure generally relates to medical monitoring systems and methods of using the same.

BACKGROUND

Medical monitoring devices are routinely used in various medical settings to obtain or measure medical parameters relating to a patient's medical condition. Many medical parameters related to a patient being monitored and measured can be presented or described by a continuous and recurring train of waveforms. Such waveforms may include, for example, $CO_2$ concentration or breathe flow rate of a patient's breath measured over time; an ECG signal measured over time, and the like. Such waveforms are produced from the cyclic breathing patterns or heart contractions (beats), respectively. Each waveform have a characteristics shape and dimensions that are a direct result of the patients physiology and state at the time of the measurement, and hence are indicative and informative to the patients' medical status, either as single waveforms or a sequential reoccurrence of waveforms over time.

Trending medical waveform parameters, such as, for example, End tidal $CO_2$ ($EtCO_2$, the maximum $CO_2$, concentration measured in a breath cycle), Respiration Rate (RR), and the like, are calculated and displayed on relevant monitors such as Capnographs, using dedicated trend screens, where, for example, the x axis is time, and y axis is the measured value (for example, the $EtCO_2$ or RR value). Such conventional trends relate traditionally to parameters (such as amplitude of the waveform or rate), which are extracted or calculated directly from the received waveform and are generally constructed using two dimensional depictions of these parameters (for example, amplitude vs. time).

Cardiopulmonary resuscitation (CPR) is performed in order to restore partial flow of oxygenated blood to the brain and heart, so as to delay tissue death and extend the brief window of opportunity for a successful resuscitation without permanent brain damage. The CPR involves a manual or mechanical series of chest compressions to create artificial blood circulation and artificial ventilation to allow blood oxygenation and $CO_2$ clearance. CPR guidelines recommend keeping a defined relatively low level of respiration rate during CPR. CPR effectiveness and potential outcome are often unknown during the resuscitation.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

Aspects of the disclosure, in some embodiments thereof, relate to devices, system and methods for providing a decision support tool during CPR by monitoring $CO_2$ waveforms and determining the efficacy and outcome of the CPR.

Advantageously, the disclosed device, system and method for determining the efficacy and/or outcome of the CPR are configured to integrate $CO_2$ related features or trends of these features together with patient's parameters/variables and to provide a care giver a tool that will allow him/her to decide how to proceed with the CPR or even whether or not to terminate it.

According to some embodiments, there is provided a decision support system for cardiopulmonary resuscitation (CPR), the system includes: a medical monitoring device configured to produce $CO_2$ waveforms of exhaled breath of a subject undergoing CPR, and a computing unit configured to: extract one or more features related to the $CO_2$ and/or a trend thereof of waveforms produced by the device, obtain one or more parameters/variables selected from a group of one or more background parameters, one or more physiological variables and one or more baseline parameters related to the subject undergoing CPR, and determine effectiveness of CPR and/or CPR predicted outcome based at least on the extracted one or more features and/or the trend thereof and on the one or more parameters/variables.

According to some embodiments, the system may further include an indication unit configured to provide an indication to a care giver regarding the effectiveness of the CPR and/or the CPR outcome. According to some embodiments, the indication unit includes a display unit configured to display the trend of more than one $CO_2$ waveform related feature and the indication regarding the effectiveness of the CPR and/or the CPR outcome.

According to some embodiments, the system may further include a mechanical chest compression device. According to some embodiments, the system may further include a chest impedance monitoring device.

According to some embodiments, there is provided herein a method for decision support during cardiopulmonary resuscitation (CPR), the method includes: producing $CO_2$ waveforms of exhaled breath of a subject undergoing CPR, extracting one or more features related to the $CO_2$ waveforms and/or a trend thereof, obtain one or more parameters/variables selected from a group of one or more background parameters, one or more physiological variables and one or more baseline parameters related to the subject undergoing CPR, and determining effectiveness of CPR and/or CPR outcome based at least on the extracted one or more features and/or the trend thereof and on the one or more parameters/variables.

According to some embodiments, the method may further include providing an indication to a care giver regarding the effectiveness of the CPR and/or the CPR outcome. According to some embodiments, the method may further include displaying, on a display unit, the trend of more than one $CO_2$ waveform related features and the indication regarding the effectiveness of the CPR and/or the CPR outcome. According to some embodiments, the method may further include treating the subject with a mechanical chest compression device and/or monitoring chest impedance during the CPR.

According to some embodiments, the one or more background parameters may include: the subject's gender, age, background disease, smoking habits, administered medication prior to CPR, prior administration of a layperson life support treatment, or any combination thereof. Each option may present a separate embodiment.

According to some embodiments, the one or more physiological variables may include: pupils' size, changes in pupils' size, difference between the two pupils' size, gasping, sweating, body temperature, changes in body temperature, tremor, color, changes in color, presenting heart rhythm, administered medication during CPR, or any combination thereof. Each option may present a separate embodiment.

According to some embodiments, the one or more the one or more baseline parameters may include: cause of cardiac arrest, time of no-flow, time of low flow, cardiac arrest being witnessed or unwitnessed. Each option may present a separate embodiment. The term flow, according to some embodiments, may refer to blood flow.

According to some embodiments, the CPR outcome may include percentage (%) of return of spontaneous circulation (ROSC), percentage (%) of long term survival, brain function or any combination thereof.

According to some embodiments, the computing unit may further be configured to determine a need to continue the CPR and/or to change one or more CPR parameters based on the determined effectiveness of CPR, CPR predicted outcome, or both.

According to some embodiments, the CPR parameter may include compression frequency, depth of compression, CPR type or any combination thereof.

According to some embodiments, there are provided methods and systems for the determination, identification and extraction of various features (parameters) of medically, time resolved waveforms, analysis thereof and their trend presentation over time.

According to some embodiments, the methods and systems provided herein may be used for the depiction and calculation of a trend of waveform related features/parameters which may be extracted from a train of medical waveforms, thereby allowing the detection or indication of the condition and status of a given patient, being monitored. In some embodiments, the methods and systems may further be used to identify patterns of the waveform related parameters trends and to correlate between a pattern and a medical status of the patient. In some embodiments, the method and systems may further be used, during manual or mechanical CPR, to identify patterns of the waveform and/or related parameters trends and to correlate between the patterns/parameters/trends, background parameters of the patient, physiologic variables of the subject and/or baseline parameters of the subject and resuscitation of the subject.

In some embodiments, various pattern recognition algorithms may be performed upon the trends to determine if a pattern can be identified and/or a correlation of the identified pattern to a given medical situation can be made. According to some embodiments, the pattern recognition algorithms may be performed upon the trends to determine if a pattern can be identified and/or a correlation of the identified pattern with resuscitation of the patient. In some embodiments the methods and systems disclosed herein further take use of various calculation tools, such as pattern finding algorithms and other tools for extracting, marking, zoom in, detecting and/or identifying known or new patient health related conditions, as indicated by the waveform feature related trends.

Thus, the methods and systems disclosed herein advantageously provide the health care provider with an efficient, accurate and time saving system for analyzing and evaluating the medical condition of the patient, such as his respiratory status, cardiac status, resuscitation and the like.

Each waveform have a characteristics shape and dimensions that are a direct result of the patients physiology and state at the time of the measurement, and hence are indicative and informative to the patients' medical status. For example, the shape and dimension of the waveform may be indicative of the efficiency of resuscitation of the patient. Using the systems and methods disclosed herein, a more accurate assessment of the medical status of the patient is reliably accessed, by identifying, determining and providing a trend analysis over time of various waveform related parameters. By utilizing the systems and methods disclosed herein, the health care provider can better sense what parameters are recurring and dominant, which parameters are changing or erratic in nature, which parameters are producing patterns over time, and the like. This additional information provided by the systems and methods disclosed herein advantageously provide a far more reliable and accurate assessment of the patients' status as opposed to analyzing a single waveform or several sequential waveforms individually (as is generally observed on a standard monitor screen of a medical monitoring device).

Additionally, as opposed to conventional trends, which are traditionally related to parameters that are extracted or calculated directly from the received waveform (parameters such as, amplitude or rate) and are generally constructed using two dimensional depictions of these parameters (for example, amplitude vs. time), the trends provided by the methods and systems disclosed herein are of various waveforms related parameters which are attributed, calculated and/or extracted from various elements of the waveform (such as the shape of the waveform) and not merely of changes to the waveform overtime. By providing such trend data of those waveform related parameter, such as characteristics of the waveforms, their shapes, and interrelations there between, in two or more dimensions provides an enhanced tool for evaluating, indicating and diagnosing a patient status.

Further, with respect to displaying waveform related parameters that are related to the shape of the waveform and/or changes thereto, the methods and systems provided herein advantageously provide the health care provider with detection and analysis of information buried" in the waveform shape, which is not readily available otherwise and cannot be simply derived from the display of the waveform itself. The methods and systems further advantageously provide the health care provider with additional valuable information regarding the patient status, which are derived from the waveform such as, detection of patterns, dominance or changes over time and the like, which otherwise cannot be simply detected or identified.

According to some embodiments, there is provided a medical monitoring system for identifying a trend of waveform related features, the system includes: a medical monitoring device configured to produce waveforms of a measured medical parameter of a patient; a computing unit configured to identify and extract one or more features related to the waveforms produced by the device, and produce a trend of the one or more waveform related features; and a display unit configured to display the trend of the one or more waveform related features.

According to some embodiments, the medical parameter of the patient is $CO_2$ in exhaled breath.

According to some embodiments, the waveform is a $CO_2$ related waveform.

According to some embodiments, the one or more waveform related features are selected from shape factors and scale factors. In some embodiments, the shape factors are selected from: up-rising slope of a CO2 waveform; the extent of the up-rising slope, the shape of the up-rising slope, the down-stroke slope of a CO2 waveform, the extent of the down stroke slope, the shape of the down stroke slope, and combinations thereof. According to some embodiments, the scale factors are selected from: width of the waveform, time between sections of the waveform, amplitude, and combinations thereof.

In some embodiments, the $CO_2$ waveform related feature is selected from: $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, a change in breath to breath correlation, a $CO_2$ duty cycle, a change in $CO_2$ duty cycle, minute ventilation, a change in minute ventilation, and combinations thereof.

In some embodiments, the computing unit is further configured to apply a pattern recognition algorithm to identify recurring pattern within the trend of the waveform related features.

In some embodiments, the trend of the waveform related feature is indicative of the health condition of the patient. In some embodiments, the trend of the waveform related feature is indicative of resuscitation efficiency and/or resuscitation outcome.

In some embodiments, the display unit is configured to display the trend of more than one waveform related feature in one trend display.

According to some embodiments, the medical monitoring device is a capnograph.

According to some embodiments, there is provided a method for identifying a trend of a medical waveform related feature, the method includes: a) extracting one or more features of the waveform; b) detecting the change of the one or more features over time to create a trend of the one or more features of the trend; and c) displaying the identified trend.

In some embodiments, the method further includes an additional step of determining resuscitation efficiency and/or predicting resuscitation outcome. In some embodiments, the medical waveform in the method is a CO2 related waveform. In some embodiments, the one or more waveform related features are selected from shape factors and scale factors. In some embodiments, the shape factors are selected from up-rising slope of a CO2 waveform; the extent of the up-rising slope, the shape of the up-rising slope, the down-stroke slope of a CO2 waveform, the extent of the down stroke slope, the shape of the down stroke slope, and combinations thereof. In further embodiments, the scale factors are selected from width of the waveform, time between sections of the waveform, amplitude, and combinations thereof. In some embodiments, the CO2 waveform related feature is selected from: EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, a change in breath to breath correlation, a CO2 duty cycle, a change in CO2 duty cycle, minute ventilation, a change in minute ventilation, and combinations thereof.

In some embodiments, the method may further include a step of identifying a recurring pattern within the trend of the waveform related features.

In further embodiments the pattern is identified by one or more of: neural networks, Support vector machines, decision trees, k-nearest-neighbor, radial-basis networks, Raves classifier, Linear discriminant analysis, Linear regression, Hidden Markov Models, K-means clustering, mixture models, Bayesian networks, fuzzy logic, ID3 and C4.5 algorithms, and combinations thereof.

In some embodiments, the method may further include displaying the trend of more than one waveform related feature in a single trend display.

According to some embodiments, the terms "subject" and "patient" may be used interchangeable.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed descriptions.

DETAILED DESCRIPTION

Figure 1:
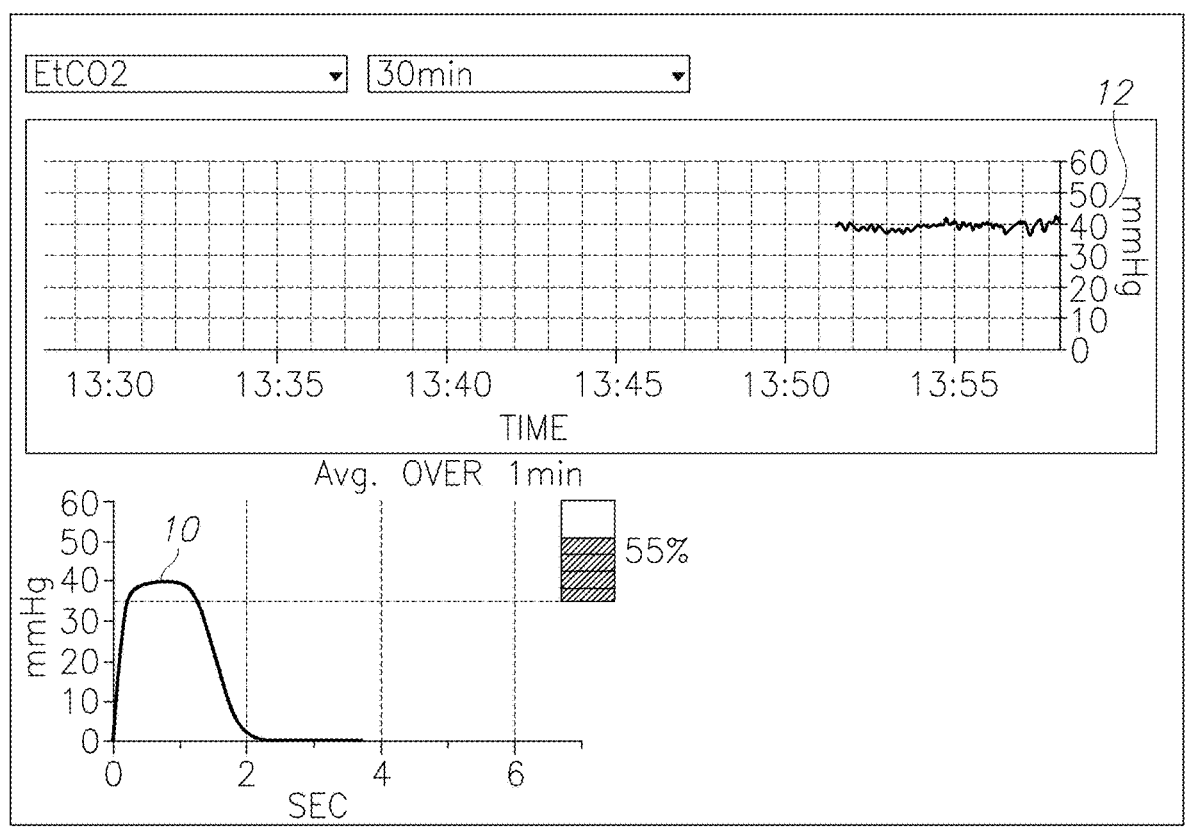
FIG. 1—a schematic representation of an exemplary display of a trend of a respiration waveform related feature and a representative waveform, according to some embodiments.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

As referred to herein, the terms "user", "medical user", "health care provider" and "health care professional" may interchangeably be used. The terms may include any health care provider who may treat and/or attend to a patient. A user may include, for example, a nurse, respiratory therapist, physician, anesthesiologist, and the like. In some cases, a user may also include a patient.

As referred to herein, the terms "device", "monitoring device" and "medical device" may interchangeably be used.

As referred to herein, the terms "patient" and "subject" may interchangeably be used and may relate to a subject being monitored by any monitoring device for any physical-condition related parameter and/or health related parameter.

As referred to herein, the terms "resuscitation", "cardio-pulmonary resuscitation" and "CPR" may be used interchangeably and refer to bringing back someone who is unconscious, not breathing, or close to death to a conscious or active state. According to some embodiments, the terms refer to the emergency procedure performed in an effort to manually preserve intact brain function until further measures are taken to restore spontaneous blood circulation and breathing in a person who is in cardiac arrest.

As referred to herein, according to some embodiments, the terms "efficacy of resuscitation" and "effectiveness of resuscitation" may be used interchangeably and may be assigned a number, such as a unit-less index, for example, on the range of 1 to 10, 1 representing inefficient resuscitation and 10 representing the most efficient resuscitation.

As referred to herein, according to some embodiments, the term "CPR predicted outcome" may represent the chances of survival immediately after resuscitation, the chances of long term survival (e.g., after 1 year, 1-5 years or any other time period after CPR), the chances of loss of memory, the chances of impaired brain function, or the like or any combination thereof.

As referred to herein, the terms ordinary, normal, typical, standard and common may interchangeably be used.

As referred to herein, the term "waveform" is directed to a recurring graphic shape which may be realized by measuring a physiological parameter of a subject over time, such as, for example, concentration of $CO_2$ in breath, flow rate of breath, electrocardiogram (ECG), pletyhsmograph, and the like. In some embodiments, a waveform is a medically, time resolved waveform. A waveform may have various characteristic parameters/features/factors that may be derived from the shape, dimension, rate or frequency, reoccurrences, and the like, and combinations thereof. In some embodiments, a feature extracted from the waveform is referred to herein as a "waveform related feature", "feature of the waveform", "waveform related parameter", "parameter related to the waveform" or "waveform related factor".

The term "Representative Waveform" is directed to a calculated single waveform that is produced by analyzing a set of waveforms and factors thereof, and defining a single waveform that is representative of the waveforms.

As referred to herein, the terms "waveform groups" or "waveform sets" relate to a sequential set of at least two waveforms.

As referred to herein, the terms "scaling factor(s)" or "scalar factor(s)" relate to measures of a waveform dimensions (such as, amplitude, width, time between sections of waveform and the like). In some embodiments, a scaling factor may be a waveform related feature.

As referred to herein, the term "shape factor(s)" relate to measures or characteristics related to the shape of the waveform (for example, slopes, curvatures, area under curve, and the like). In some embodiments, the shape factors may be a waveform related feature.

As referred to herein, the terms "rate factor(s)" or "frequency factor(s)" relate to measures of the waveform recurrence, the rate of change of the waveform, rate of change of the scaling or shape factors. In some embodiments, each of the rate factors may be a characteristic parameter/feature of the waveform.

As referred to herein, the term "pattern(s)": relates to any identified/determined pattern over time, which is recurring, known or unknown, that may be produced when graphically displaying any of the waveforms or waveforms related factors/parameters. In some embodiments, a pattern may be predefined. In some embodiments, a pattern may determined if it is clearly repeating itself for a given number of times (for example, 2-10 times), over a given period of time (for example, 30-1200 seconds). For example, a pattern is determined if it is clearly repeating itself at least twice over a given period of time As referred to herein, the term "$EtCO_2$" relates to End tidal $CO_2$. The $CO_2$ is exhaled out of the body and the concentration of the exhaled $CO_2$, also known as end tidal $CO_2$ ($EtCO_2$) is an approximate estimation of the alveolar $CO_2$ pressure and thus of the arterial levels of $CO_2$. The values of EtCO2 may be measured in units of pressure, such as, for example, mmHg.

As referred to herein, the term "breath cycle" includes the stages of exhalation and inhalation. The breath cycle may be derived from a $CO_2$ waveform which depicts the change in expired $CO_2$ Volume over time, ($EtCO_2$). During a breath cycle, the levels of $CO_2$ initially increase as a result of $CO_2$ release from the airways, from what is known as the "dead space", which is the space in which no gas exchange takes place. Then, the $CO_2$ rapidly reaches a plateau at high levels of $CO_2$, which corresponds to the release of $CO_2$ from the lungs, in the exhalation phase. A rapid decline in exhaled $CO_2$ proceeds the inhalation phase, characterized by absence/minute levels of $CO_2$.

According to some embodiments, the terms "calculated" and "computed" may interchangeably be used.

According to some embodiments, there is provided a method for identifying a trend of waveform related features, the method includes extracting one or more features of the waveform, and detecting the change of the one or more features over time to create a trend of the one or more features of the trend; and displaying the identified trend.

According to some embodiments, the method further includes an additional step of determining resuscitation efficiency and/or predicting resuscitation outcome.

According to some embodiments, there is provided a system for identifying and displaying a trend of waveform related features, the system includes a medical monitoring device configured to produce a waveform of a medical parameter of a patient; a computing unit configured to identify and extract one or more features related to the waveform and produce a trend of the one or more waveform related features; and a display unit configured to display the trend of the one or more waveform related features.

According to some embodiments, the system is further configured to identify a resuscitation efficiency of the patient based produced trend. According to some embodiments, the waveform is a medical waveform of a physiological parameter of a patient being monitored. In some embodiments, the waveform is obtained/measured by a medical device measuring and/or analyzing a medical parameter of the patient. In some embodiments, the medical parameter is respiration (for example, as measured by $CO_2$ concentration in exhaled breath), heart rate, and the like, or combinations thereof.

According to some embodiments, a medical waveform is a waveform related to respiration, and can be obtained by capnography. In capnography, a capnograph collects samples of a patient's breath, senses and calculates the real time $CO_2$ concentration (as partial $CO_2$ pressure) of the sample. The calculated $CO_2$ concentration over time is depicted on an appropriate display as a moving waveform (also referred to as capnogram). The resolution of the moving waveform and the sweep time are such that a user can identify breath cycles on the display. The information obtained in capnography may be used to determine a condition of a patient.

According to some embodiments, there is provided a system for identifying and displaying a trend of a respiration waveform related features, the system includes a capnograph configured to produce a waveform of $CO_2$ concentration in exhaled breath of a patient over time; a computing unit (processor) configured to identify and extract one or more features related to the waveform and produce a trend of the one or more waveform related features; and a display unit configured to display the trend of the one or more waveform related features. In some embodiments, the system may further provide information regarding additional breath related parameters, such as, for example, breathe rate, and further provide a trend thereof.

According to some embodiments, the system is further configured to identify a resuscitation efficiency of the patient based produced trend. According to some embodiments, the system is further configured to determine the need to continue the CPR and/or to change a CPR parameter based on the determined CPR efficiency and/or the produced trend. According to some embodiments, the CPR parameter may include CPR frequency, CPR type (e.g. mouth-to-mouth and chest compressions, chest compressions only), depth of compression or any combination thereof. Each possibility is a separate embodiment.

According to some embodiments, there is provided a method for identifying and displaying a trend of a respiration waveform related feature(s), the method includes extracting one or more features of the waveform, and detecting the change of the one or more features over time to create a trend of the one or more features of the trend; and displaying the identified trend.

According to some embodiments, the method further includes an additional step of identifying resuscitation and/or resuscitation efficiency of the patient. According to some embodiments, the method further includes determining the need to continue the CPR and/or to change a CPR parameter based on the determined CPR efficiency and/or the produced trend. According to some embodiments, the CPR parameter may include CPR frequency, CPR type (e.g. mouth-to-mouth and chest compressions, chest compressions only), depth of compression or any combination thereof. Each possibility is a separate embodiment.

According to some embodiments, there is provided a method for use in a system for identifying and displaying a trend of medical waveform related features, the system includes a medical monitoring device configured to produce a waveform of a medical parameter of a patient; a computing unit configured to identify and extract one or more features related to the waveform and produce a trend of the one or more waveform related features; and a display unit configured to display the trend of the one or more waveform related features.

According to some embodiments, there is provided a method used in a system for identifying and displaying a trend of a respiration waveform related features, the system includes a capnograph configured to produce a waveform of $CO_2$ concentration in exhaled breath of a patient over time; a computing unit (processor) configured to identify and extract one or more features related to the waveform and produce a trend of the one or more waveform related features; and a display unit configured to display the trend of the one or more waveform related features.

According to some embodiments, a waveform can be characterized by two types of factors, namely shape factors and by scale factors. Shape factors characterize and/or describe the shape or pattern of the waveform. A shape factor may include, for example, parameters of a non-linear function describing an upstroke of the waveform. Scale factors are the waveform values and/or ratios, for example, height, width, width at half-height, duty cycle, or any other value or combination of values.

According to some embodiments, the waveform related features may be selected from scale factors and shape factors.

According to some embodiments, the medical waveform is a CO2 waveform. In some embodiments, the CO2 waveform may be obtained by a capnograph. In some embodiments, a typical, $CO_2$ waveform is a curve which represents the varying $CO_2$ levels throughout the respiratory cycle. In phase I, which represents the end of respiration, CO2 level is zero. Next, as exhalation begins, a sloped upstroke is observed (Phase II). Follows is a gradual rise (Phase III), a plateau having a peak just before a point which marks the end of exhalation. This is followed by a sharp down-stroke back to zero (inspiration, Phase IV), which is followed by a clean inspiration period.

According to some embodiments, a shape factor feature of a $CO_2$ waveform may be selected from, but not limited to: the up-rising slope of a $CO_2$ waveform; the extent of the slope, the shape of the slope, the down stroke slope, extent of the down stroke slope, the shape of the down stroke slope, and like.

In some embodiments, a trend of slope features of a waveform can be obtained by the systems and methods disclosed herein, by extracting such features from the waveform analyzing their occurrence and/or frequency and/or distribution over time to produce a trend of the features. By analyzing, producing and displaying the trend of these features, a reliable and enhanced means that can aid the health care provider in assessing or assisting in diagnosing the patient status (for example, severe, moderate, light or even differentiating between artifact and real) is obtained, since looking at any individual waveform, could not be used to indicate a patient condition nor severity.

According to some embodiments, a patient with asthma (or in some cases even a patient not having asthma) can have both "normal" and "sloped" waveforms. But looking at a trend of the waveforms features, their dominance; patterns thereof, a measure of slope extent and/or shape over time, provide stronger evidence and indication to the patient's condition and can be used to a greater advantage for monitoring the treatment of the patient.

According to some embodiments, a patient having a cardiac arrest and undergoing CPR can have a breathing pattern, and thus $CO_2$ waveforms, which can be indicative of the efficiency of the CPR. According to some embodiments, looking at the waveforms features, their trends, their dominance; patterns thereof, a measure of slope extent and/or shape over time, while taking into account parameters/ variables of the patient (such as, but not limited to, subject's gender, age, background disease, smoking habits, cause of cardiac arrest, prior administration of a layperson life support treatment, presenting heart rhythm, time of no-flow, time of low flow, body temperature, cardiac arrest being witnessed or unwitnessed, administered medication or any combination thereof), provide stronger evidence and indication to the efficiency of the CPR. According to some embodiments, evaluation of the waveforms features, their trends, their dominance; patterns thereof, a measure of slope extent and/or shape over time, while taking into account background parameters, physiologic parameters/variables and/or baseline parameters/variables of the patient, may be predictive of the outcome of the CPR. According to some embodiments, evaluation of the waveforms features, their trends, their dominance; patterns thereof, a measure of slope extent and/or shape over time, while taking into account background parameters, physiologic parameters/variables and/or baseline parameters/variables of the patient, may be indicative of the need to change, continue or discontinue the CPR of the patient.

According to some embodiments, a scale factor feature of the waveform may be selected from, but not limited to: amplitude, the variability of the amplitude, mean of the amplitude, dispersion of the amplitude, width of the waveform, the variability of the wave form, mean of the waveform, dispersion of the waveform, time between sections of the waveform, the variability of the time between sections of the waveform, mean of the time between sections of the waveform, dispersion of the time between sections of the waveform, Inhalation to Exhalation Ratio, variability of the Inhalation to Exhalation Ratio, mean of the Inhalation to Exhalation Ratio, dispersion of the Inhalation to Exhalation Ratio, and the like.

According to some embodiments, the $CO_2$ waveform related feature may be selected from, but not limited to: $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, a change in breath to breath correlation, a $CO_2$ duty cycle, a change in $CO_2$ duty cycle, minute ventilation, a change in minute ventilation, the I:E ratio and changes thereto, the variability of one or more of the $CO_2$ waveform related features; the measure of the variability; the correlation between two or more $CO_2$ waveform related features, the correlation between two or more $CO_2$ waveform related features and other breath related parameters, (for example, correlation of area under the curve (convolution) with breath flow rate), and the like, or any combination thereof. Each possibility is a separate embodiment.

According to some embodiments, the trend data of the waveform related features may be derived from a single waveform or a train of waveforms. In some embodiments, the trend data of the waveform related features may be derived from the shape factor or scale factor or rate factors that have been evaluated to be dominant over a given set of waveforms. In some embodiments, the trend data of the waveform related features may be derived from the shape factor or scale factor of a representative waveform.

According to some embodiments, the methods disclosed herein can further be used to correlate one or more of the trend features over time with additional medical parameters, such as, for example, but not limited to: blood pressure, medication, depth of sleep, desaturation, medication, and the like. In some embodiments, the collected information may be used to better evaluate the condition of the patient and may be used to improve medical related decisions, such as, for example, with respect to weaning, sedation, and the like. In some embodiments, the collected information may be used to better evaluate the condition of the patient and may be used to improve medical related decisions, such as, for example, with respect to CPR duration, frequency, use of defibrillation, defibrillation parameters and the like.

According to some embodiments, the methods and systems disclosed herein further provide for pattern recognition, by searching and detecting patterns of recurring events, which may be indicative of a given condition. Such pattern recognition can be used to detect known or unknown patterns with the trend data of the waveform related features. The pattern recognition may be performed by the processing unit. In some embodiments, the processing unit includes an analyzing unit (an analyzer) configured to utilize a various algorithms to identify and/or calculate a pattern of the trend of the waveform related features.

In some embodiments, the pattern recognition can be used to detect known patterns or patterns that are less known but have been observed for the given patient class (for example, patient under a given condition or clinical environment or clinical procedure), or for the specific patient.

In some embodiments, the patterns identified can be defined according to established, known patterns (such as, for example, with respect to monitoring of respiration: Kossmaul breathing, Biot's respiration, Cluster breathing, Cheyne Stokes respiration, and the like). In some embodiments, the patterns identified can be defined in accordance with their identification in real time or off-line (i.e., not while the patient is being monitored and the waveform related features are analyzed and presented).

According to some embodiments, the patterns thus identified can be attributed to classes of patient's clinical or therapeutic status (for example, with respect to monitoring of respiration, if the patient is during weaning, if the patient is under SIMV ventilation mode, and the like).

According to some embodiments, the pattern identification, recognition and/or discovery can be performed by various supervised and unsupervised methods and algorithms, such as, for example, but not limited to: neural networks, Support vector machines, decision trees, k-nearest-neighbor, radial-basis networks, Raves classifier, Linear discriminant analysis, Linear regression, Hidden Markov Models, K-means clustering, mixture models, Bayesian networks, fuzzy logic, ID3 and C4.5 algorithms, and combinations thereof. Each possibility is a separate embodiment.

According to some embodiments, the system may further include a display unit (such as a monitor) configured to display the trend of the waveform related feature(s). In some embodiments, the display unit may display a trend of one or more waveform related parameters. When displaying the trend of more than one waveform related features, the displayed trends may be displayed simultaneously. The trends may be visually separated by shape (for example, columns, circles, dots, and the like); display pattern (for example, solid, empty, full, patterned); display color; display icons, and the like. In some embodiments, the presented trends may be further marked based on their physiological relevance. For example, with respect to respiration monitoring, trends of features which are indicative or related to obstructive or restrictive breathing; hyperventilation or hypoventilation; Cheyne stokes; and the like may, each be differentially presented in accordance with its respective physiological relevance. In some embodiments, the trend(s) may be displayed together with presentation of additional medical parameters, such as, for example, a medical waveform. In some embodiments, the display unit may further display any parameter useful for the health care provider in tracking the patient's breath and medical condition. In some embodiments, such parameters may be selected from, but not limited to: electrocardiogram, electroencephalogram, electrogastrogram, electromyogram, heart rate signals, pathological sounds, ultrasound, or any other suitable medical parameter. In some embodiments, the display unit may be integrally formed with the monitoring device. In some embodiments, the display unit may be functionally connected to the device.

According to some embodiments, the system may further include a user interface or a controller, that may allow the user to select the data to be displayed and/or to control various operating parameters. In some embodiments, the user may select which waveform related features are to be analyzed and/or trended. In some embodiments, the user may select which waveform related feature trends are displayed. In some embodiments, the user may select a time frame over which the trend is calculated or displayed. In some embodiments, the user may "zoom in" on a selected region of the trend. In some embodiments, the user may select which patterns are displayed and/or tracked. In some embodiments, various different displays may be included in the system to accommodate different needs of different users (such as a nurse, a physician, an anesthesiologist, and the like). Allowing the user to change the view of the waveform related features trend, may permit the user to toggle through the different levels of information for further evaluation of a condition. In further embodiments, the user interface may also allow the user to enter characteristic information for each patient. In some embodiments, the user interface may allow browsing capability that allows scrolling throughout the data over time. In some embodiments, the user interface may allow marking of events of interest for future evaluation.

Reference is now made to FIG. 1, which is a schematic representation of an exemplary display of a respiration waveform related feature trend and a representative waveform according to which the waveform related feature trend is determined. As shown in FIG. 1, the bottom panel displays a representative $CO_2$ waveform (10), as determined according to the measurement of $CO_2$ in exhaled breath ($EtCO_2$) of the patient being monitored. The representative waveform illustrated shows the concentration of $CO_2$ (mmHg) in exhaled breath over time (seconds). The time scale from the representative waveform is in the order of 5 to 10 seconds, as is common for the period of a breath. In the upper panel, a trend display (12) of the waveform related parameter (in this example, $EtCO_2$, measured in units of mmHg) is presented. The time scale of the trend display can be chosen at any time range, such as, for example, for 1-60 minutes (such as, for example, for 1, 5, 10, 20, 30 minutes), or for 1-24 hours (such as, for example, 1, 2, 6, 12 hours). Further, the user may zoom-in onto any section of the trend display in order to evaluate the fine details of the waveform related feature at any point of interest. The exemplary trend shown in FIG. 1 is of a two dimensional trend (in this example, $EtCO_2$ over time).

Figure 2:
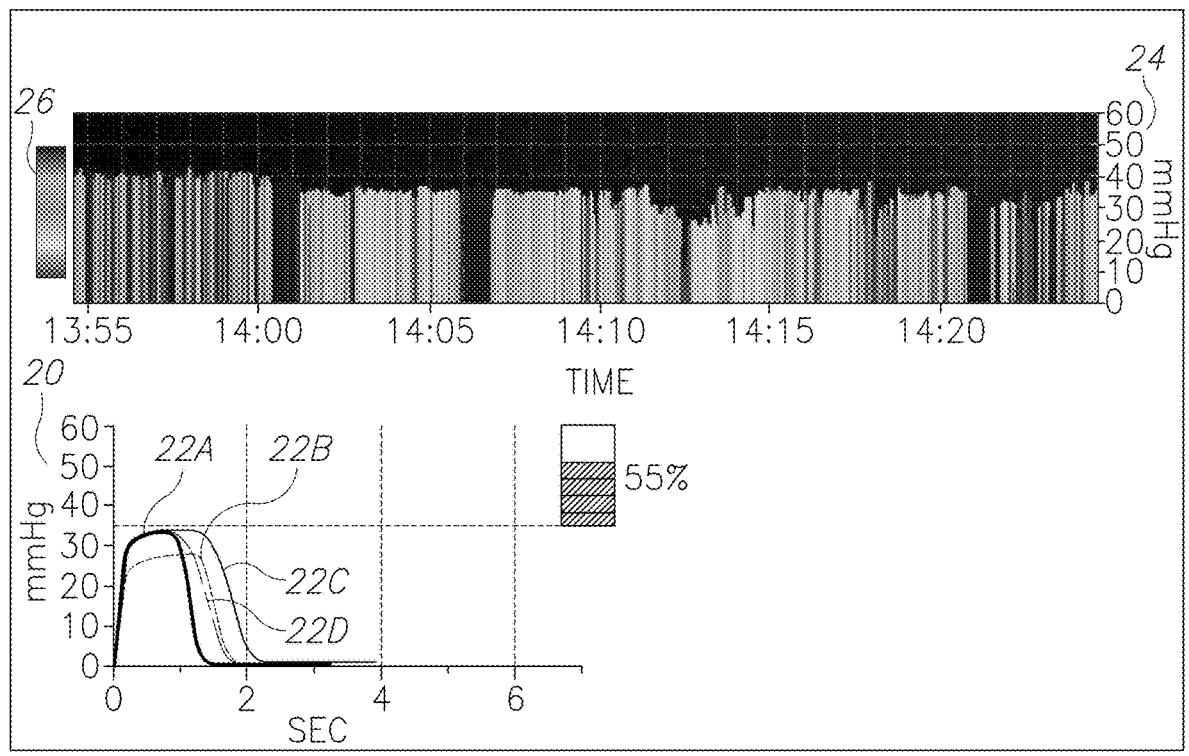
FIG. 2—a schematic representation of an exemplary display of trends of respiration waveform related features and representative waveforms, according to some embodiments.

Reference is now made to FIG. 2, which is a schematic representation of an exemplary display of trends of respiration waveform related features and representative waveforms. As shown in FIG. 2, the bottom panel (20) displays representative (recent) $CO_2$ waveforms (22C-D), as determined according to the measurement of $CO_2$ in exhaled breath ($EtCO_2$) of the patient being monitored. Further shown are baseline (reference) waveforms (22A-B) that may be selected by the health care provider. Such reference waveforms are used, for example, as a reference waveform prior to treatment, sedation, and the like. In the upper panel (24), a trend display of waveform related features is presented. The trend display in this example is the form of pillars (columns). The trend display shows several waveform related features (for example, $EtCO_2$ levels, breath width and calculated area under the curve of the waveform), wherein each of the features is represented by a different, distinct type of pillar. By different type of pillar it is meant that the pillars can be easily and readily be distinctly identified. For example, the pillars may have different colors, different shades, different shapes (for example, varying width/height of columns), different fill patterns (for example, empty, full, patterned), and the like. A code (such as a color code) correlating between the pillar and the feature it relates to may be indicated on the display, to allow the user to easily identify the various waveform related features. For example, a color may be representative of the level of area under the curve, the column (pillar) height may be representative of the $EtCO_2$ concentration and the width of the column may be representative of a measure of the breath width. As shown in FIG. 2, a color code (26, shown as gray scale code) is provided in order to interpret (represent) the scale of the depicted waveform related feature. In the example shown in FIG. 2, color code (26) is indicative of the level of area under the curve. The time period of the displayed trend can be chosen from a number of time periods (such as, for example, in the range of 1 to 60 minutes or 1 to 24 hours), and zooming in at any desired section is possible, in order to identify fine details, if so desired by the user. In some embodiments, the use of columns (pillars) to depict the waveform related features and not the waveform shapes themselves provide an easier, clearer and enhanced means that allows the health care provider to observe changes in the features and hence in the medical condition of the patient.

In some embodiments, additional waveform related parameters trends may be displayed, such that the trend of more than two features are simultaneously displayed in one trend display area, wherein each of the trends is easily distinguishable from the other. For example, additional waveform related feature may be the width of the exhalation period. For example, additional waveform related parameter may be the width of the inhalation period. Thus, in such example, the trend of four separate and distinct waveform related features may be simultaneously displayed in one trend display.

In some embodiments, the values of the trend of each of the waveform related features may be calculated from each individual waveform measured or calculated from a representative waveform.

Figure 3:
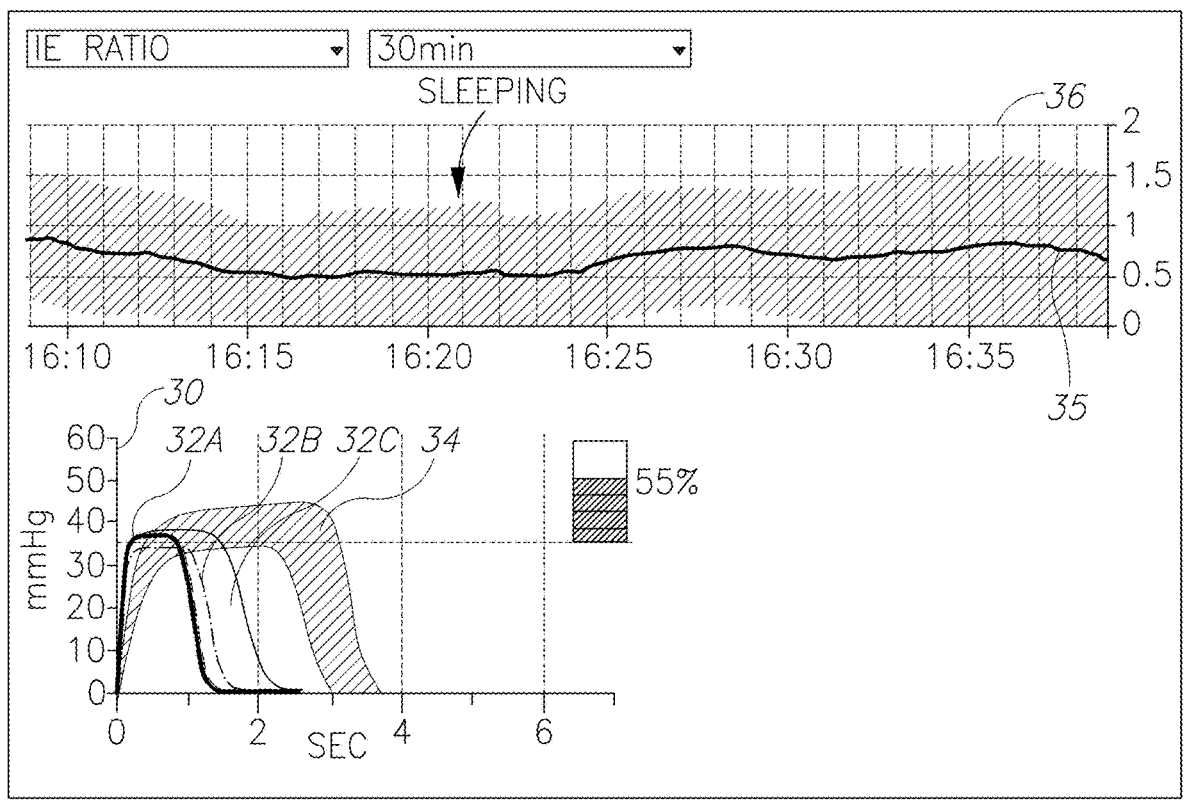
FIG. 3—a schematic representation of an exemplary display of trends of respiration waveform related features and representative waveforms, according to some embodiments.

Reference is now made to FIG. 3, which is a schematic representation of an exemplary display of trends of respiration waveform related features and representative waveforms. As shown in FIG. 3, the bottom panel (30) displays representative $CO_2$ waveform (32A), as determined according to the measurement of $CO_2$ in exhaled breath ($EtCO_2$) of the patient being monitored (mmHg/time(Sec)). Also shown are individual recent waveforms of recent measured breaths (32B-C). Further shown are reference waveform ranges (34, "Textbook"), of normal healthy patients, for providing a comparison means that may be used by the health care provider to simplify identification of pathological conditions. In the upper panel, a trend display (36) of waveform related features is presented. The trend display in this example is the form of a line (35) showing the average inhalation to exhalation ratio (I to E) over time, with the standard derivation depicted as shadowed area. The average I:E ratio and the standard deviation thereof may be calculated by various means, such as, for example, for an average of 2 or more breaths; over a given period of time; and the like. The average can be a running average or a continuous average. The values of the features may be calculated based on the individual waveform or the representative waveform. The trend display may further simultaneously display additional one or more features, such as, the respiration rate. The various trend of the features displayed may be visually distinguishable by varying thickness of the trend line, varying color of the trend line and the like. For example, the line may represent to I:E ratio and varying thickness or color of the line is representative of the respiration rate, or vice versa. Thus, in such example, several waveform related parameters, which physiologically relate to each other, may be simultaneously displayed in one graph. Further, in the example presented in FIG. 3, a health care provider can readily and relatively simply differentiate between, for example, systematic and erratic breathing pattern.

Figure 4:
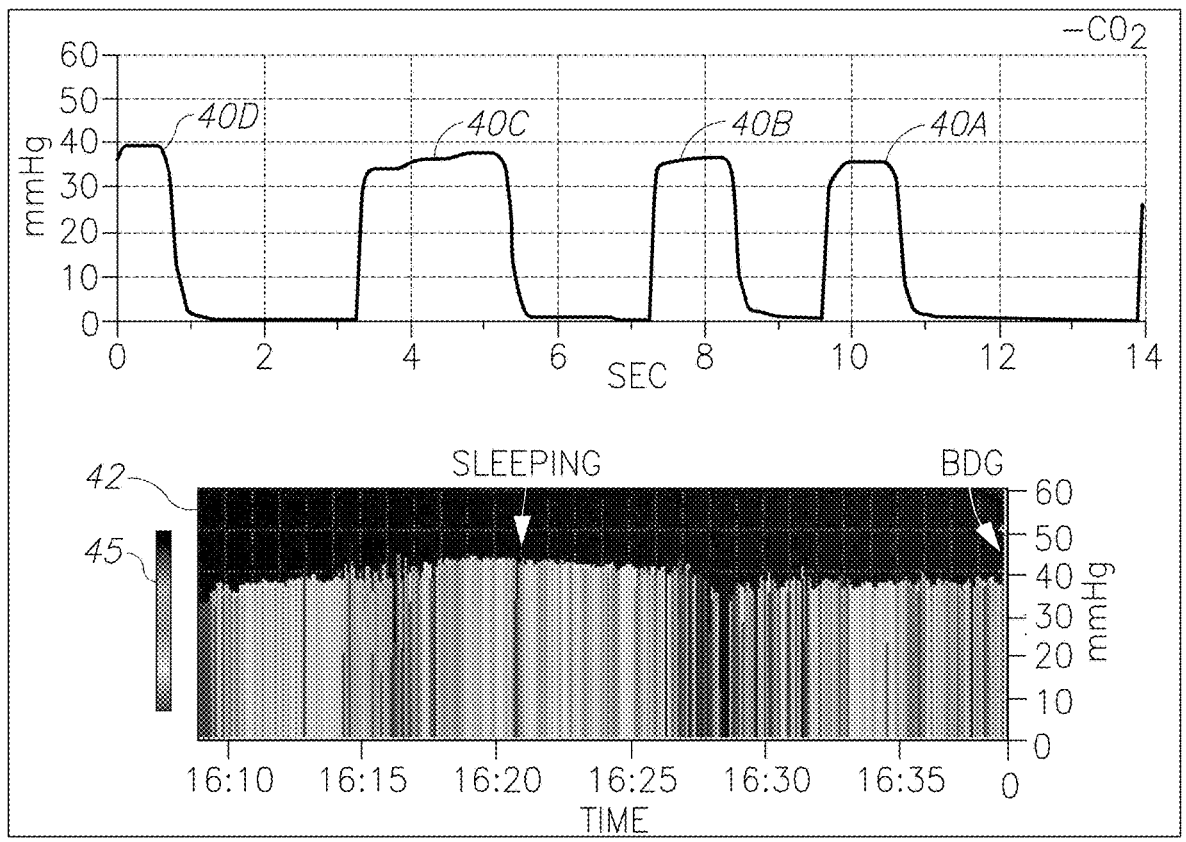
FIG. 4—a schematic representation of an exemplary display of trends of respiration waveform related features and representative waveforms, according to some embodiments.

Reference is now made to FIG. 4, which is a schematic representation of an exemplary display of trends of respiration waveform related features and representative waveforms. As shown in FIG. 4, the upper panel displays advancing instantaneous $CO_2$ waveforms (40A-D), as determined according to the measurement of $CO_2$ in exhaled breath ($EtCO_2$) of the patient being monitored (mmHg/time(Sec)). The trend information (42) is displayed in the lower panel. The trend information is shown in the form of columns, each representing a different waveform related feature, wherein the features in this example are related to the shape of the waveform. The columns are visually distinct (for example, by color, shade, width of column, shape of column, etc.). For example, the amplitude of the column represents the slope feature of the waveform and the color of the column represents the area under the curve. By this mode of display, the dominance or frequency extent of a waveform shape of interest is readily identifiable. A code (such as a color code (45)) correlating between the pillar and the feature it relates to may be indicated on the display, to allow the user to easily identify the various waveform related features. In addition, various additional medical parameters may further be depicted and presented. The additional medical parameters may be depicted manually (for example, by the health care provider) or automatically. In the example shown in FIG. 4, parameters such as "Sleeping" and "BDG" (which stands for blood gas) are depicted, to indicate their occurrence.

According to some embodiments, if in addition to the data from a capnograph (i.e. concentration of $CO_2$), additional medical information is provided, for example, regarding breath flow, additional useful information can be calculated and depicted. For example, if an integral of the flow pattern overtime is made with the CO2 concentration over time, a measure of the relative volume of expired CO2 can be calculated and depicted. The additional data can be used to evaluate changes or trends in minute ventilation. Trends of shallow breathing can also be noted, where rapid shallow breathing is used as a useful parameter and indicator during weaning process.

Figure 5A:
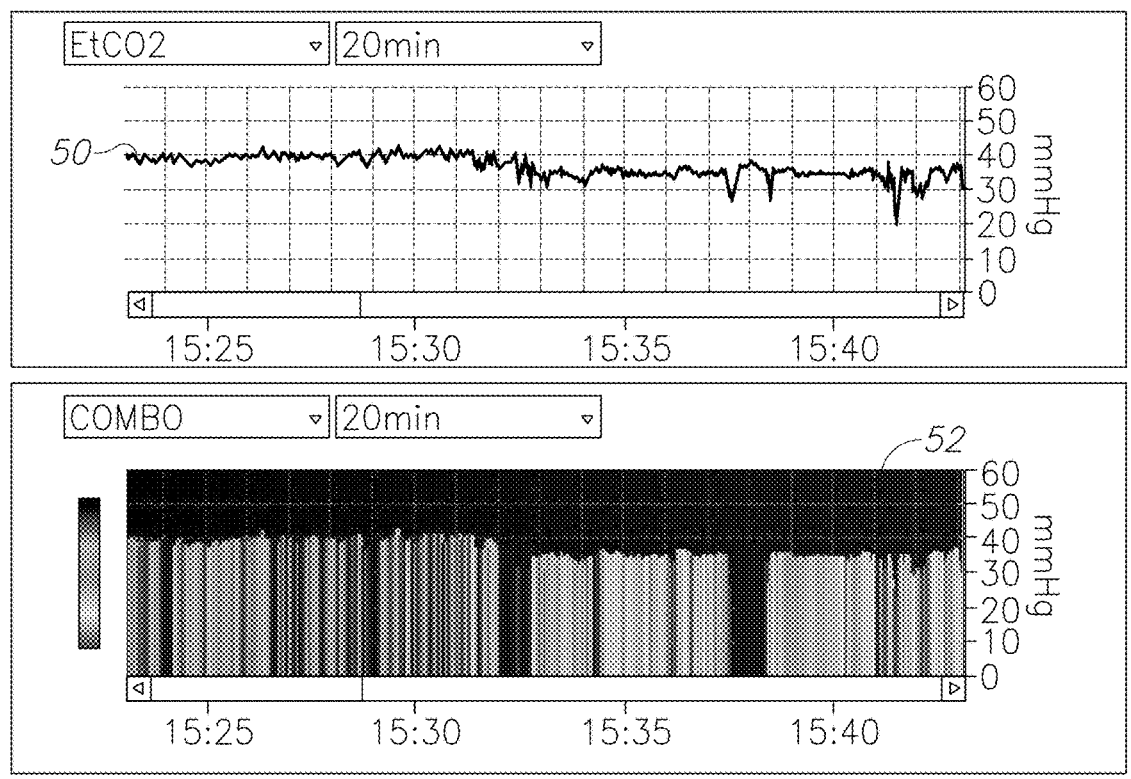
FIGS. 5A-B—schematic representations of exemplary displays of trends of respiration waveform related features that are shown in parallel, according to some embodiments.
Figure 5B:
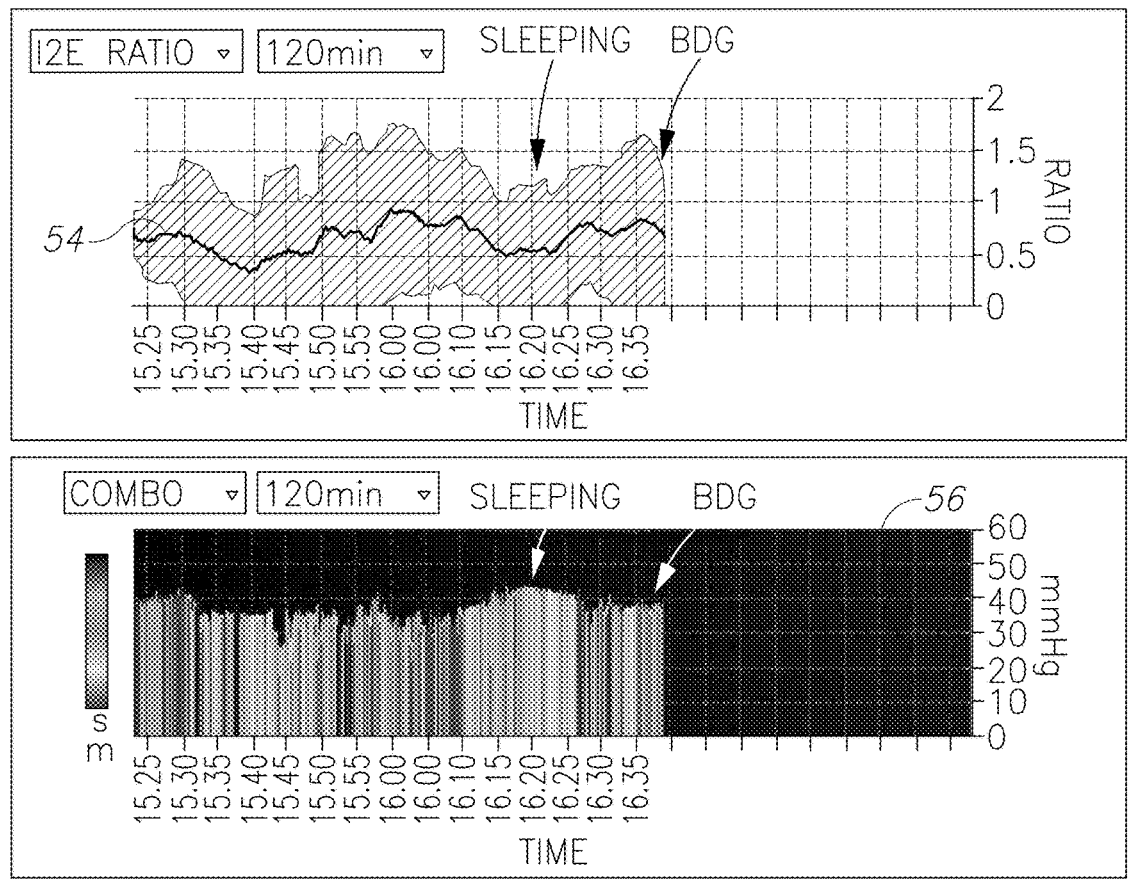

Reference is now made to FIGS. 5A-B, which are schematic representations of exemplary displays of trends of respiration waveform related features that can be shown in parallel. As shown in FIG. 5A, the upper panel shows the trend of the $EtCO_2$ feature over short period of time (in this example, 20 minutes), in the form of a line (50). The lower panel of FIG. 5A shows the trends of the EtCo2, area under the curve and the I:E ratio in the form of columns ((52), wherein the features are identified based on the color of the column). As shown in FIG. 5B, the upper panel presents the trend of the I:E ratio over a longer period of time (in this example, 120 minutes) in the form of a line (54). The lower panel of FIG. 5B shown the trends of the I:E ratio and the $EtCO_2$ in the form of columns ((56) with area under the curve defined by color. The two displays (FIG. 5A and FIG. 5B) may be simultaneously displayed in parallel in order to permit comparison of various features at similar times, and further allow identification of events that can be relates and shown together with multi pieces of information. In addition, various additional medical parameters may further be depicted and presented. The additional medical parameters may be depicted manually (for example, by the health care provider) or automatically. Such exemplary medical paremeters (as shown in FIG. 5B), are "sleeping", and "BDG" (Blood Gas).

According to some embodiments, the trend display allows the option of "zooming in" on any time point(s) of the trend, to identify the actual parameter on which that trend was determined at the indicated time point(s). For example, when zooming in on the trend at a designated time point, the representative waveform which was observed at the same time point can be seen. According to further embodiments, scanning the trends too can be made simultaneous with the representative waveform. In some exemplary embodiments, additionally or alternatively to the presentation of an instantaneous moving waveform on the screen, a visualization of the lungs breathing (depicted, for example, by an animated cartoon of the lungs), whereby the rate of the breathing may be proportional to the present respiration rate (RR), and the size is relative to EtCO2, with optionally additional color code, indicative of the respiratory health of the patient.

Figure 6:
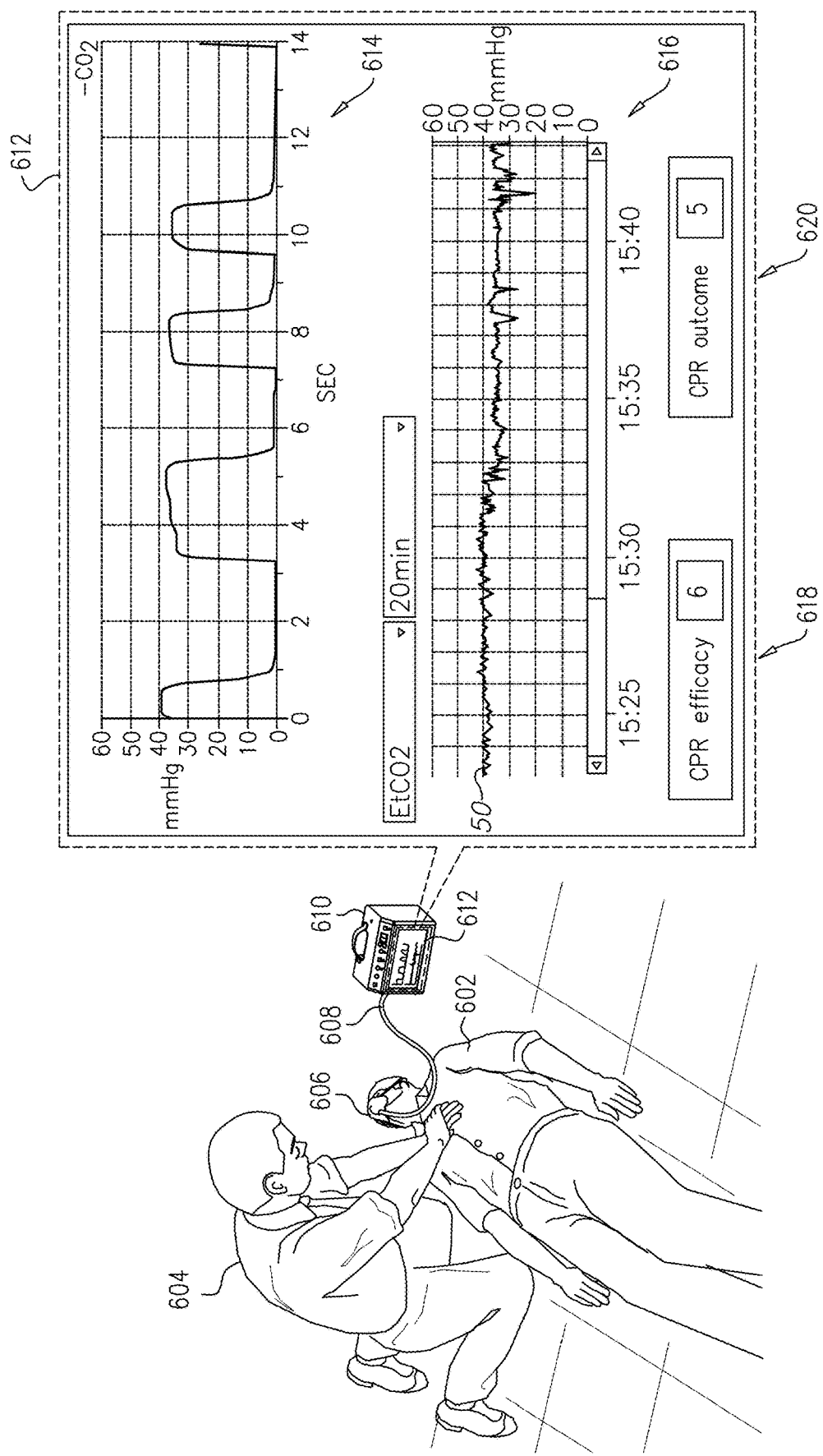
FIG. 6—schematic representations of a subject receiving CPR with a decision support system, according to some embodiments.

Reference is now made to FIG. 6, which is a schematic representation of a subject receiving CPR with a decision support system, according to some embodiments. As shown in this figure, a subject (602) is lying on the ground and receiving CPR by a care giver (604). Subject (602) is wearing a mask (606) which collects exhaled breath through a tube (608). The collected breath samples are transferred, through tube (608), to a capnograph (not shown), which is a part of a decision support system (610). Decision support system (610) includes a monitor (612) that provides care giver (604) or any other care giver information about the respiratory status of subject (602), for example, $CO_2$ waveform series (614), a trend display (616) of the waveform related parameter (in this example, $EtCO_2$, measured in units of mmHg), CPR efficacy score (618) and CPR predicted outcome score (620). CPR efficacy score (618) and CPR predicted outcome score (620) may be calculated by a processor (also being a part of decision support system (610) using information obtained from the waveform measurements, for example, from a trend of a $CO_2$ related parameter, and information such as, background, physiologic and/or baseline parameters/variables of subject (602) (for example, gender, age, cause of cardiac arrest, medication administered, witnessed/unwitnessed cardiac arrest of subject (602) etc.). Information presented on monitor (612) may be helpful to care giver (604) in making a decision on how and if the CPR should proceed.

It is understood by the skilled in the art that the processor of the system is configured to implement the method as essentially described herein.

In the description and claims of the application, each of the words "comprise" "include" and "have", and forms thereof, are not necessarily limited to members in a list with which the words may be associated.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What is claimed is:

1. A decision support system for cardiopulmonary resuscitation (CPR) for determination of whether to continue CPR, to change a CPR parameter or both, based upon CPR efficiency, the system comprising:
   a medical monitoring system configured to produce carbon dioxide ($CO_2$) waveforms representative of a concentration of $CO_2$ in exhaled breath of a subject undergoing CPR, wherein the $CO_2$ waveforms are generated using a capnograph comprising a $CO_2$ sensor; and
   a processor configured to:
      extract one or more features related to the $CO_2$ waveforms, wherein the one or more features comprises a shape of the $CO_2$ waveforms over time; and
      determine an $EtCO_2$ trend in the one or more extracted features related to the $CO_2$ waveforms, wherein the trend, together with one or more parameters/variables selected from any of one or more background parameters, one or more physiological variables comprising: pupils' size, changes in pupils' size, difference between the two pupils' size, gasping, sweating, body temperature, changes in body temperature, tremor, color, changes in color, presenting heart rhythm, administered medication during CPR, or any combination thereof, and one or more baseline parameters related to the subject undergoing CPR, is associated with CPR efficiency; and
   a display configured to display the trend and to display an indication of CPR efficiency.

2. The system of claim 1, wherein the display is configured to display a CPR efficacy score associated with the CPR efficiency.

3. The system of claim 1, further comprising a mechanical chest compression device.

4. The system of claim 1, further comprising a chest impedance monitoring device.

5. The system of claim 1, wherein the processor is configured to account for one or more background parameters to determine whether to continue CPR, to change a CPR parameter, or both, wherein the one or more background parameters comprises: the subject's gender, age, background disease, smoking habits, administered medication prior to CPR, prior administration of a layperson life support treatment, or any combination thereof.

6. The system of claim 1, wherein the processor is configured to account for one or more physiological variables associated with the subject to determine whether to continue CPR, to change a CPR parameter, or both, wherein the one or more physiological variables comprises: pupils' size, changes in pupils' size, difference between the two pupils' size, gasping, sweating, body temperature, changes in body temperature, tremor, color, changes in color, presenting heart rhythm, administered medication during CPR, or any combination thereof.

7. The system of claim 1, wherein the processor is configured to account for one or more baseline parameters to determine whether to continue CPR, to change a CPR parameter, or both, wherein the one or more baseline parameters comprises: cause of cardiac arrest, time of no-flow, time of low flow, cardiac arrest being witnessed or unwitnessed.

8. The system of claim 1, wherein the shape of the $CO_2$ waveforms are shape factors selected from: up-rising slope of a $CO_2$ waveform, the extent of the up-rising slope, the shape of the up-rising slope, the down-stroke slope of a $CO_2$ waveform, the extent of the down stroke slope, the shape of the down stroke slope, or any combinations thereof.

9. The system of claim 1, wherein the processor is configured to extract one or more features related to the $CO_2$ waveforms, wherein the one or more features comprises a shape of the $CO_2$ waveforms and a dimension of the $CO_2$ waveforms over time.

10. The system of claim 9, wherein the dimension of the $CO_2$ waveforms are scale factors selected from: width of the waveform, time between sections of the waveform, amplitude, or any combinations thereof.

11. The system of claim 1, wherein the processor is further configured to apply a pattern recognition algorithm to identify recurring patterns within the trend.

12. The system of claim 1, wherein the CPR parameter comprises compression frequency, depth of compression, CPR type, or any combination thereof.

13. The system of claim 2, wherein the CPR efficiency score is a unit-less index value between 1 and 10, wherein 1 represents inefficient resuscitation and 10 represents most efficient resuscitation.

14. The system of claim 11, wherein the processor is configured to correlate the recurring pattern with resuscitation of the subject.

15. A method for decision support during cardiopulmonary resuscitation (CPR), the method comprising:
   producing carbon dioxide ($CO_2$) waveforms representative of a $CO_2$ concentration in exhaled breath of a subject undergoing CPR, wherein the $CO_2$ waveforms are generated using a capnograph comprising a $CO_2$ sensor;
   extracting, using a processor, one or more features related to the $CO_2$ waveforms, wherein the one or more features comprises a shape factor of the $CO_2$ waveforms;
   determining, using the processor, an $EtCO_2$ trend in the one or more extracted features related to the $CO_2$ waveforms, wherein the trend is indicative of a medical status of the subject;
   determining, using the processor, an index value indicative of an efficiency of CPR based on the trend, together with one or more parameters/variables selected from any of one or more background parameters, one or more physiological variables comprising: pupils' size, changes in pupils' size, difference between the two pupils' size, gasping, sweating, body temperature, changes in body temperature, tremor, color, changes in color, presenting heart rhythm, administered medication during CPR, or any combination thereof, and one or more baseline parameters related to the subject undergoing CPR; and
   determining, using the processor, whether to continue CPR, to change a CPR parameter, or both based on the medical status of the subject and the index value.

16. The method of claim 15, wherein the one or more features comprises a shape factor of the $CO_2$ waveforms and a scale factor of the $CO_2$ waveforms.

17. The system of claim 15, further comprising displaying, on a display, the index value.

18. The method of claim 15, further comprising treating the subject with a mechanical chest compression device and/or monitoring chest impedance during the CPR.

19. The method of claim 15, the comprising accounting, using the processor, for one or more background parameters to determine whether to continue CPR, to change a CPR parameter, or both, wherein the one or more background parameters comprises: the subject's gender, age, background disease, smoking habits, administered medication prior to CPR, prior administration of a layperson life support treatment, or any combination thereof.

20. The method of claim 15, comprising accounting, using the processor, for one or more physiological variables associated with the medical status of the subject to determine whether to continue CPR, to change a CPR parameter, or both, wherein the one or more physiological variables comprises: pupils' size, changes in pupils' size, difference between the two pupils' size, gasping, sweating, body temperature, changes in body temperature, tremor, color, changes in color, presenting heart rhythm, administered medication during CPR, or any combination thereof.

21. The method of claim 15, comprising accounting, using the processor, for one or more baseline parameters related to the subject to determine whether to continue CPR, to change a CPR parameter, or both, wherein the one or more baseline parameters comprises: cause of cardiac arrest, time of no-flow, time of low flow, cardiac arrest being witnessed or unwitnessed.

22. The method of claim 15, wherein the index value is between 1 and 10, wherein 1 represents inefficient resuscitation and 10 represents most efficient resuscitation.

23. The method of claim 15, comprising identifying, using the processor, a recurring pattern in the trend.

24. The method of claim 23, correlating the recurring pattern with the medical status of the subject.

* * * * *